(12) United States Patent
Olah et al.

(10) Patent No.: US 8,212,088 B2
(45) Date of Patent: *Jul. 3, 2012

(54) EFFICIENT AND SELECTIVE CHEMICAL RECYCLING OF CARBON DIOXIDE TO METHANOL, DIMETHYL ETHER AND DERIVED PRODUCTS

(75) Inventors: George A. Olah, Beverly Hills, CA (US); G. K. Surya Prakash, Hacienda Heights, CA (US)

(73) Assignee: University of Southern California, Los Angeles, CA (US)

(*) Notice: Subject to any disclaimer, the term of this patent is extended or adjusted under 35 U.S.C. 154(b) by 510 days.

This patent is subject to a terminal disclaimer.

(21) Appl. No.: 12/537,647

(22) Filed: Aug. 7, 2009

(65) Prior Publication Data

US 2009/0293348 A1     Dec. 3, 2009

Related U.S. Application Data

(63) Continuation of application No. 11/766,408, filed on Jun. 21, 2007, now Pat. No. 7,608,743, which is a continuation-in-part of application No. 11/402,050, filed on Apr. 12, 2006, now Pat. No. 7,605,293.

(60) Provisional application No. 60/671,651, filed on Apr. 15, 2005, provisional application No. 60/763,678, filed on Jan. 30, 2006.

(51) Int. Cl.
  *C07C 29/51* (2006.01)
  *C07C 29/15* (2006.01)
  *C07C 29/132* (2006.01)

(52) U.S. Cl. ........................ 568/884; 568/885

(58) Field of Classification Search .................. 568/884, 568/885
  See application file for complete search history.

(56) References Cited

U.S. PATENT DOCUMENTS

| | | | |
|---|---|---|---|
| 2,787,631 A | 4/1957 | Stevens | 558/277 |
| 3,236,762 A | 2/1966 | Rabo et al. | 208/111.25 |
| 3,482,952 A | 12/1969 | Sieg et al. | 44/449 |
| 3,711,258 A | 1/1973 | Adams et al. | 585/733 |
| 4,364,915 A | 12/1982 | Proctor | 423/437.1 |
| 4,374,288 A | 2/1983 | Scragg | 568/910 |
| 4,607,127 A | 8/1986 | Spencer | 568/482 |
| 4,618,732 A | 10/1986 | Gesser et al. | 568/910.5 |
| 4,705,771 A | 11/1987 | Spencer | 502/255 |
| 4,762,528 A | 8/1988 | Reichl | 44/51 |
| 4,891,049 A | 1/1990 | Dillon et al. | 44/387 |
| 5,349,096 A | 9/1994 | Cockman et al. | 568/896 |
| 5,510,393 A | 4/1996 | Coffman | 518/703 |
| 5,571,483 A | 11/1996 | Pfingstl et al. | 422/166 |
| 5,599,638 A | 2/1997 | Surampudi et al. | 429/33 |
| 5,606,107 A | 2/1997 | Smith | 562/17 |
| 5,753,143 A | 5/1998 | Bhat et al. | 252/373 |
| 5,928,806 A | 7/1999 | Olah et al. | 429/13 |
| 6,045,761 A | 4/2000 | Bill et al. | 422/186.04 |
| 6,170,264 B1 | 1/2001 | Viteri et al. | 60/671 |
| 6,232,352 B1 | 5/2001 | Vidalin | 518/700 |
| 6,375,832 B1 | 4/2002 | Eliasson et al. | 208/141 |
| 6,376,254 B1 | 4/2002 | Bather et al. | 436/140 |
| 6,531,630 B2 | 3/2003 | Vidalin | 562/519 |
| 6,690,180 B2 | 2/2004 | Schwartz et al. | 324/670 |
| 6,740,434 B2 | 5/2004 | Surampudi et al. | 429/15 |
| 6,782,947 B2 | 8/2004 | de Rouffignac et al. | 166/245 |
| 6,881,759 B2 | 4/2005 | Nielsen et al. | 518/705 |
| 7,081,547 B2 | 7/2006 | Fujimoto et al. | 560/232 |
| 7,288,387 B2 | 10/2007 | Cheng et al. | 435/67 |
| 7,375,142 B2 | 5/2008 | Pearson | 518/706 |
| 7,378,561 B2 | 5/2008 | Olah et al. | 568/885 |
| 7,459,590 B2 | 12/2008 | Olah et al. | 568/885 |
| 2006/0235088 A1 | 10/2006 | Olah et al. | 518/702 |
| 2006/0235091 A1 | 10/2006 | Olah et al. | 518/726 |
| 2007/0254969 A1 | 11/2007 | Olah et al. | 518/726 |
| 2008/0039538 A1 | 2/2008 | Olah et al. | 518/702 |

FOREIGN PATENT DOCUMENTS

| | | |
|---|---|---|
| EP | 1 180 511 A1 | 2/2002 |
| FR | 2 877 939 A1 | 5/2006 |
| JP | 2004-285187 A | 10/2004 |
| RU | 2104990 C1 | 2/1998 |

OTHER PUBLICATIONS

Ashby et al., "Concerning the Formation of Hydrogen in Nuclear Waste. Quantitative Generation of Hydrogen via a Cannizzaro Intermediate," J. Am. Chem. Soc. 115: 1171-1173 (1993).
International Search Report, application No. PCT/US2006/013742, dated Aug. 14, 2006.

*Primary Examiner* — Elvis O Price
(74) *Attorney, Agent, or Firm* — Winston & Strawn LLP

(57) ABSTRACT

An efficient and environmentally beneficial method of recycling and producing methanol from varied sources of carbon dioxide including flue gases of fossil fuel burning powerplants, industrial exhaust gases or the atmosphere itself. Converting carbon dioxide by chemical or electrochemical reduction seconardy treatment to produce essentially methanol, dimethyl ether and derived products.

20 Claims, 2 Drawing Sheets

EFFICIENT AND SELECTIVE CHEMICAL RECYCLING OF CARBON DIOXIDE TO METHANOL, DIMETHYL ETHER AND DERIVED PRODUCTS

CROSS-REFERENCE TO RELATED APPLICATIONS

This application is a continuation of application Ser. No. 11/766,408 filed Jun. 21, 2007 now U.S. Pat. 7,608,743, which is a continuation-in-part of application Ser. No. 11/402,050 filed Apr. 12, 2006 now U.S. Pat. No.7,605,293, which claims the benefit of provisional applications 60/671,651 filed Apr. 15, 2005 and 60/763,678 filed Jan. 30, 2006. The content of each application is expressly incorporated herein by reference thereto.

BACKGROUND

Hydrocarbons are essential in modern life. Hydrocarbons are used as fuel and raw material in various fields, including the chemical, petrochemical, plastics, and rubber industries. Fossil fuels, such as coal, oil and gas, are composed of hydrocarbons with varying ratios of carbon and hydrogen, and is non-renewably used when combusted, forming carbon dioxide and water. Despite their wide application and high demand, fossil fuels present a number of disadvantages, including the finite reserve, irreversible combustion and contribution to air pollution and global warming. Considering these disadvantages, and the increasing demand for energy, alternative sources of energy are needed.

One such alternative frequently mentioned is hydrogen, and the so-called "hydrogen economy." Hydrogen is beneficial as a clean fuel, producing only water when combusted. Free hydrogen, however, is not a natural energy source, and its generation from hydrocarbons or water is a highly energy-consuming process. Further, when hydrogen is produced from hydrocarbons, any claimed benefit of hydrogen as a clean fuel is outweighed by the fact that generation of hydrogen itself, mainly by reforming of natural gas, oil or coal to synthesis gas ("syn-gas") a mixture of CO and $H_2$, is far from clean. It consumes fossil fuels, with a quarter of the energy of the fuel being lost as heat. Hydrogen is also not a convenient energy storage medium because it is difficult and costly to handle, store, transport and distribute. As it is extremely volatile and potentially explosive, hydrogen gas requires high-pressure equipment, costly and non-existent infrastructure, special materials to minimize diffusion and leakage, and extensive safety precautions to prevent explosions.

It was suggested that a more practical alternative is methanol. Methanol, $CH_3OH$, is the simplest liquid oxygenated hydrocarbon, differing from methane ($CH_4$) by a single additional oxygen atom. Methanol, also called methyl alcohol or wood alcohol, is a colorless, water-soluble liquid with a mild alcoholic odor, and is easy to store and transport. It freezes at −97.6° C., boils at 64.6° C., and has a density of 0.791 at 20° C.

Methanol is not only a convenient and safe way to store energy, but, together with its derived dimethyl ether (DME), is an excellent fuel. Dimethyl ether is easily obtained from methanol by dehydration and is an effective fuel particularly in diesel engines because of its high cetane number and favorable properties. Methanol and dimethyl ether can be blended with gasoline or diesel and used as fuels, for example in internal combustion engines or electricity generators. One of the most efficient use of methanol is in fuel cells, particularly in direct methanol fuel cell (DMFC), in which methanol is directly oxidized with air to carbon dioxide and water while producing electricity.

Contrary to gasoline, which is a complex mixture of many different hydrocarbons and additives, methanol is a single chemical compound. It contains about half the energy density of gasoline, meaning that two liters of methanol provides the same energy as a liter of gasoline. Even though methanol's energy content is lower, it has a higher octane rating of 100 (average of the research octane number (RON) of 107 and motor octane number (MON) of 92), which means that the fuel/air mixture can be compressed to a smaller volume before being ignited. This allows the engine to run at a higher compression ratio (10-11 to 1 against 8-9 to 1 of a gasoline engine), more efficiently than a gasoline-powered engine. Efficiency is also increased by methanol's higher "flame speed," which enables faster, more complete fuel combustion in the engines. These factors explain the high efficiency of methanol despite its lower energy density than gasoline. Further, to render methanol more ignitable even under the most frigid conditions, methanol can be mixed with gasoline, with volatile compounds (e.g., dimethyl ether), with other components or with a device to vaporize or atomize methanol. For example, an automotive fuel can be prepared by adding methanol to gasoline with the fuel having a minimum gasoline content of at least 15% by volume (M85 fuel) so that it can readily start even in low temperature environments M20 fuel (with 20% added methanol to gasoline) is presently introduced in China. Of course, any replacement of gasoline in such fuels will conserve oil resources, and the amount of methanol to add can be determined depending upon the specific engine design.

Methanol has a latent heat of vaporization of about 3.7 times higher than gasoline, and can absorb a significantly larger amount of heat when passing from liquid to gas state. This helps remove heat away from the engine and enables the use of an air-cooled radiator instead of a heavier water-cooled system. Thus, compared to a gasoline-powered car, a methanol-powered engine provides a smaller, lighter engine block, reduced cooling requirements, and better acceleration and mileage capabilities. Methanol is also more environment-friendly than gasoline, and produces low overall emissions of air pollutants such as hydrocarbons, $NO_x$, $SO_2$ and particulates.

Methanol is also one of the safest fuels available. Compared to gasoline, methanol's physical and chemical properties significantly reduce the risk of fire. Methanol has lower volatility, and methanol vapor must be four times more concentrated than gasoline for ignition to occur. Even when ignited, methanol burns about four times slower than gasoline, releases heat only at one-eighth the rate of gasoline fire, and is far less likely to spread to surrounding ignitable materials because of the low radiant heat output. It has been estimated by the EPA that switching from gasoline to methanol would reduce incidence of fuel-related fire by 90%. Methanol burns with a colorless flame, but additives can solve this problem.

Methanol also provides an attractive and more environment-friendly alternative to diesel fuel. Methanol does not produce smoke, soot, or particulates when combusted, in contrast to diesel fuel, which generally produces polluting particles during combustion. Methanol also produces very low emissions of NOx because it burns at a lower temperature than diesel. Furthermore, methanol has a significantly higher vapor pressure compared to diesel fuel, and the higher volatility allows easy start even in cold weather, without producing white smoke typical of cold start with a conventional diesel engine. If desired, additives or ignition improvers, such as octyl nitrate, tetrahydrofurfuryl nitrate, peroxides or higher alkyl ethers, can be added to bring methanol's cetane rating to the level closer to diesel. Methanol can also be used in the manufacture of biodiesel fuels by esterification of fatty acids.

Closely related and derived from methanol, and also a desirable alternative fuel is dimethyl ether. Dimethyl ether (DME, $CH_3OCH_3$), the simplest of all ethers, is a colorless, nontoxic, non-corrosive, non-carcinogenic and environmentally friendly chemical that is mainly used today as an aerosol propellant in spray cans, in place of the banned CFC gases. DME has a boiling point of −25° C., and is a gas under ambient conditions. DME is, however, easily handled as liquid and stored in pressurized tanks, much like liquefied petroleum gas (LPG). The interest in dimethyl ether as alternative fuel lies in its high cetane rating of 55 to 60, which is much higher than that of methanol and is also higher than the cetane rating of 40 to 55 of conventional diesel fuels. The cetane rating indicates that DME can be effectively used in diesel engines. Advantageously, DME, like methanol, is clean burning, and produces no soot particulates, black smoke or $SO_2$, and only very low amounts of $NO_x$ and other emissions even without after-treatment of its exhaust gas. Some of the physical and chemical properties DME, in comparison to diesel fuel, are shown in Table 1.

TABLE 1

Comparison of the physical properties of DME and diesel fuel

|  | DME | Diesel fuel |
| --- | --- | --- |
| Boiling point ° C. | −24.9 | 180-360 |
| Vapor pressure at 20° C. (bar) | 5.1 | — |
| Liquid density at 20° C. (kg/m$^3$) | 668 | 840-890 |
| Heating value (kcal/kg) | 6,880 | 10,150 |
| Cetane number | 55-60 | 40-55 |
| Autoignition temperature (° C.) | 235 | 200-300 |
| Flammability limits in air (vol %) | 3.4-17 | 0.6-6.5 |

Currently, DME is exclusively produced by dehydration of methanol. A method for synthesizing DME directly from synthesis gas by combining the methanol synthesis and dehydration steps in a single process has also been developed.

Another methanol derivative is dimethyl carbonate (DMC), which can be obtained by converting methanol with phosgene or by oxidative carbonylation of the methanol. DMC has a high cetane rating, and can be blended into diesel fuel in a concentration up to 10%, reducing fuel viscosity and improving emissions.

Methanol and its derivatives, e.g., DME, DMC, and biodiesel, have many existing and potential uses. They can be used, for example, as a substitute for gasoline and diesel fuel in ICE-powered cars with only minor modifications to the existing engines and fuel systems. Methanol can also be used in fuel cells, for fuel cell vehicles (FCVs), which are considered to be the best alternative to ICEs in the transportation field. DME is also a potential substitute for LNG and LPG for heating homes and in industrial uses.

U.S. Pat. No. 5,599,638 discloses a simple direct methanol fuel cell (DMFC) and addresses the disadvantages of hydrogen fuel cells. In contrast to a hydrogen fuel cell, the DMFC is not dependent on generation of hydrogen by processes such as electrolysis of water or reformation of natural gas or hydrocarbon. The DMFC is also more cost effective because methanol, as a liquid fuel, does not require cooling at ambient temperatures or costly high pressure infrastructure and can be used with existing storage and dispensing units, unlike hydrogen fuel, whose storage and distribution requires new infrastructure. Further, methanol has a relatively high theoretical volumetric energy density compared to other systems such as conventional batteries and the $H_2$-PEM fuel cell. This is of great importance for small portable applications (cellular phones, laptop computers, etc.), for which small size and weight of energy unit is desired.

The DMFC offers numerous benefits in various areas, including the transportation sector. By eliminating the need for a methanol steam reformer, the DMFC significantly reduces the cost, complexity and weight of the vehicle, and improves fuel economy. A DMFC system is also comparable in its simplicity to a direct hydrogen fuel cell, without the cumbersome problems of on-board hydrogen storage or hydrogen producing reformers. Because only water and $CO_2$ are emitted, emissions of other pollutants (e.g., $NO_x$, PM, $SO_2$, etc.) are eliminated. Direct methanol fuel cell vehicles are expected to be virtually zero emission vehicles (ZEV), and use of methanol fuel cell vehicles offers to nearly eliminate air pollutants from vehicles in the long term. Further, unlike ICE vehicles, the emission profile is expected to remain nearly unchanged over time. New membranes based on hydrocarbon or hydrofluorocarbon materials with reduced cost and crossover characteristics have been developed that allow room temperature efficiency of 34%.

Methanol as indicated provides a number of important advantages as transportation fuel. Contrary to hydrogen, methanol does not require any energy intensive procedures for pressurization or liquefaction. Because it is a liquid at room temperature, it can be easily handled, stored, distributed and carried in vehicles. It can act as an ideal hydrogen carrier for fuel cell vehicles through on-board methanol reformers, and can be used directly in DMFC vehicles.

Methanol is also an attractive source of fuel for static applications. For example, methanol can be used directly as fuel in gas turbines to generate electric power. Gas turbines typically use natural gas or light petroleum distillate fractions as fuel. Compared to such fuels, methanol can achieve higher power output and lower $NO_x$ emissions because of its lower flame temperature. Since methanol does not contain sulfur, $SO_2$ emissions are also eliminated. Operation on methanol offers the same flexibility as natural gas and distillate fuels, and can be performed with existing turbines, originally designed for natural gas or other fossil fuels, after relatively easy modification. Methanol is also an attractive fuel since fuel-grade methanol, with lower production cost than higher purity chemical-grade methanol, can be used in turbines. Because the size and weight of a fuel cell is of less importance in static applications than mobile applications, various fuel cells other than PEM fuel cells and DMFC, such as phosphoric acid, molten carbonate and solid oxide fuel cells (PAFC, MCFC, and SOFC, respectively), can also be used.

Methanol and dimethyl ether are also very convenient materials for storage and transportation of energy without the great disadvantage and potential danger of using hydrogen. Hydrogen can readily converted with $CO_2$ to methanol and/or DME thus providing a convenient safe form for storing and transporting energy produced from any source.

In addition to these uses as fuels, methanol and methanol-derived chemicals have other significant applications in the chemical industry. Today, methanol is one of the most important feedstock in the chemical industry. Most of the 32 million tons of annually produced methanol is used to manufacture a large variety of chemical products and materials, including basic chemicals such as formaldehyde, acetic acid, MTBE (although it is increasingly phased out for environmental reasons), as well as various polymers, paints, adhesives, construction materials, and others. Worldwide, almost 70% of methanol is used to produce formaldehyde (38%), methyl-tert-butyl ether (MTBE, 20%) and acetic acid (11%). Methanol is also a feedstock for chloromethanes, methylamines, methyl methacrylate, and dimethyl terephthalate, among others. These chemical intermediates are then processed to manufacture products such as paints, resins, silicones, adhesives, antifreeze, and plastics. Formaldehyde, produced in large quantities from methanol, is mainly used to prepare phenol-, urea- and melamine-formaldehyde and polyacetal resins as well as butanediol and methylene bis(4-phenyl isocyanate) (MDI; MDI foam is used as insulation in refrigerators, doors, and in car dashboards and bumpers). Formaldehyde resins are predominantly employed as an adhesive in a wide variety of applications, e.g., manufacture of particle boards, plywood and other wood panels. Examples of methanol-derived chemical products and materials are shown in FIG. 1.

In producing basic chemicals, raw material feedstock constitutes typically up to 60-70% of the manufacturing costs. The cost of feedstock therefore plays a significant economic role. Because of its lower cost, methanol is considered a potential feedstock for processes currently utilizing more expensive feedstocks such as ethylene and propylene, to produce chemicals including acetic acid, acetaldehyde, ethanol, ethylene glycol, styrene, and ethylbenzene, and various synthetic hydrocarbon products. For example, direct conversion of methanol to ethanol can be achieved using a rhodium-based catalyst, which has been found to promote the reductive carbonylation of methanol to acetaldehyde with selectivity close to 90%, and a ruthenium catalyst, which further reduces acetaldehyde to ethanol. The possibility of producing ethylene glycol via methanol oxidative coupling instead of the usual process using ethylene as feedstock is also pursued, and significant advances for synthesizing ethylene glycol from dimethyl ether, obtained by methanol dehydration, have also been made.

Conversion of methanol to olefins such as ethylene and propylene, also known as methanol to olefin (MTO) technology, is particularly promising considering the high demand for olefin materials, especially in polyolefin production. The MTO technology is presently a two-step process, in which natural gas is converted to methanol via syn-gas and methanol is then transformed to olefin. It is considered that methanol is first dehydrated to dimethyl ether (DME), which then reacts to form ethylene and/or propylene. Small amounts of butenes, higher olefins, alkanes, and aromatics are also formed.

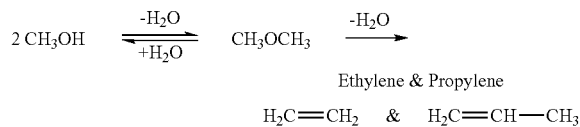

Various catalysts, e.g., synthetic aluminosilicate zeolite catalysts, such as ZSM-5 (a zeolite developed by Mobil), silicoaluminophosphate (SAPO) molecular sieves such as SAPO-34 and SAPO-17 (UOP), as well as bi-functional supported acid-base catalysts such as tungsten oxide over alumina ($WO_3/Al_2O_3$), have been found to be active in converting methanol to ethylene and propylene at a temperature between 250 and 350° C. The type and amount of the end product depend on the type of the catalyst and the MTO process used. Depending on the operating conditions, the weight ratio of propylene to ethylene can be modified between about 0.77 and 1.33, allowing considerable flexibility. For example, when using SAPO-34 according to an MTO process developed by UOP and Norsk Hydro, methanol is converted to ethylene and propylene at more than 80% selectivity, and also to butene (a valuable starting material for a number of products) at about 10%. When using an MTO process developed by Lurgi with ZSM-5 catalysts, mostly propylene is produced at yields above 70%. A process developed by ExxonMobil, with ZSM-5 catalyst, produces hydrocarbons in the gasoline and/or distillate range at selectivity greater than 95%.

There is also a methanol to gasoline (MTG) process, in which medium-pore zeolites with considerable acidity, e.g., ZSM-5, are used as catalysts. In this process, methanol is first dehydrated to an equilibrium mixture of dimethyl ether, methanol and water over a catalyst, and this mixture is then converted to light olefins, primarily ethylene and propylene. The light olefins can undergo further transformations to higher olefins, $C_3$-$C_6$ alkanes, and $C_6$-$C_{10}$ aromatics such as toluene, xylenes, and trimethylbenzene.

Olah has developed independently MTO and MTG process using supported bifunctional acid-base non zeolitic catalysts. With decreasing oil and gas reserves, it is inevitable that synthetic hydrocarbons would play a major role. Thus, methanol-based synthetic hydrocarbons and chemicals available through MTG and MTO processes will assume increasing importance in replacing oil and gas-based materials. The listed uses of methanol is only illustrative and not limiting.

Methanol besides mentioned and other related uses can also be used as a source of single cell proteins. A single cell protein (SCP) refers to a protein produced by a microorganism which degrades hydrocarbon substrates while gaining energy. The protein content depends on the type of microorganism, e.g., bacteria, yeast, mold, etc. The SCP has many uses, including uses as food and animal feed.

Considering the numerous uses of methanol, it is clearly desirable to have improved and efficient methods of producing methanol. Currently, methanol is almost exclusively made from synthesis gas obtained from incomplete combustion (or catalytic reforming) of fossil fuel, mainly natural gas (methane) and coal.

Methanol can also be made from renewable biomass, but such methanol production also involves syn-gas and may not be energetically favorable and limited in terms of scale. As used herein, the term "biomass" includes any type of plant or animal material, i.e., materials produced by a life form, including wood and wood wastes, agricultural crops and their waste byproducts, municipal solid waste, animal waste, aquatic plants, and algae. The method of transforming biomass to methanol is similar to the method of producing methanol from coal, and requires gasification of biomass to syn-gas, followed by methanol synthesis by the same processes used with fossil fuel. Use of biomass also presents other disadvantages, such as low energy density and high cost of collecting and transporting bulky biomass. Although recent improvements involving the use of "biocrude," black liquid obtained from fast pyrolysis of biomass, is somewhat promising, more development is needed for commercial application of biocrude.

The presently existing method of producing methanol involves syn-gas. Syn-gas is a mixture of hydrogen, carbon monoxide and carbon dioxide, and produces methanol over a heterogeneous catalyst according to the following equations:

The first two reactions are exothermic with heat of reaction equal to −21.7 kcal.mol$^{-1}$ and −9.8 kcal.mol$^{-1}$, respectively, and result in a decrease in volume. Conversion to methanol is favored by increasing the pressure and decreasing the temperature according to Le Chatelier's principle. The third equation describes the endothermic reverse water gas shift reaction (RWGSR). Carbon monoxide produced in the third reaction can further react with hydrogen to produce methanol.

Synthesis gas for methanol production can be obtained by reforming or partial oxidation of any carbonaceous material, such as coal, coke, natural gas, petroleum, heavy oil, and asphalt. The composition of syn-gas is generally characterized by the stoichiometric number S, corresponding to the equation shown below.

$$S = \frac{(\text{moles } H_2 - \text{moles } CO_2)}{(\text{moles } CO + \text{moles } CO_2)}$$

Ideally, S should be equal to or slightly above 2. A value above 2 indicates excess hydrogen, while a value below 2 indicates relative hydrogen deficiency. Reforming of feedstock having a higher H/C ratio, such as propane, butane or naphthas, leads to S values in the vicinity of 2, ideal for conversion to methanol. When coal or methane is used, however, additional treatment is required to obtain an optimal S value. Synthesis gas from coal requires treatment to avoid formation of undesired byproducts. Steam reforming of methane yields syn-gas with a stoichiometric number of 2.8 to 3.0, and requires lowering the S value closer to 2 by adding $CO_2$ or using excess hydrogen in some other process such as ammonia synthesis. However, natural gas is still the preferred feedstock for methanol production because it offers high hydrogen content and, additionally, the lowest energy consumption, capital investment and operating costs. Natural gas also contains fewer impurities such as sulfur, halogenated compounds, and metals which may poison the catalysts used in the process.

The existing processes invariably employ extremely active and selective copper-based catalysts, differing only in the reactor design and catalyst arrangement. Because only part of syn-gas is converted to methanol after passing over the catalyst, the remaining syn-gas is recycled after separation of methanol and water. There is also a more recently developed liquid phase process for methanol production, during which syn-gas is bubbled into liquid. Although the existing processes have methanol selectivity greater than 99% and energy efficiency above 70%, crude methanol leaving the reactor still contains water and other impurities, such as dissolved gas (e.g., methane, CO, and $CO_2$), dimethyl ether, methyl formate, acetone, higher alcohols (ethanol, propanol, butanol), and long-chain hydrocarbons. Commercially, methanol is available in three grades of purity: fuel grade, "A" grade, generally used as a solvent, and "AA" or chemical grade. Chemical grade has the highest purity with a methanol content exceeding 99.85% and is the standard generally observed in the industry for methanol production. The syn-gas generation and purification steps are critical in the existing processes, and the end result would largely depend on the nature and purity of the feedstock. To achieve the desired level of purity, methanol produced by the existing processes is usually purified by sufficient distillation. Another major disadvantage of the existing process for producing methanol through syn-gas is the energy requirement of the first highly endothermic steam reforming step. The process is also inefficient because it involves transformation of methane in an oxidative reaction to carbon monoxide (and some $CO_2$), which in turn must be reduced to methanol.

It is highly desirable and advantageous to produce methanol without first producing syn-gas. It would be further advantageous to use an abundant, practically unlimited resource such as carbon dioxide via its chemical recycling as the carbon source to produce methanol. For example, U.S. Pat. No. 5,599,638, the entire content of which is incorporated herein by reference thereto, discloses production of methanol, and related oxygenates and hydrocarbons, based on a carbon dioxide-based regenerative fuel cell concept.

When hydrocarbons are burned they produce carbon dioxide and water. It is of great significance, if this process can be reversed and an efficient and economic process can be found to produce methanol from carbon dioxide and water to be subsequently used for energy storage, fuels and production of synthetic hydrocarbons. In plant photosynthesis, carbon dioxide is captured from the air and converted with water and solar energy into new plant life. Conversion of plant life into fossil fuel, however, is a very long process. Thus, it is highly desirable to develop a process for chemical recycling carbon dioxide to produce hydrocarbon in a short, commercially feasible time scale.

Carbon dioxide is known to be photochemically or electrochemically readily reduced to formic acid with formaldhyde and methanol being formed in only smaller amounts. Direct electrochemical reduction of $CO_2$ into methanol under pressure also provides methyl formate. Catalytic hydrogenation of carbon dioxide with hydrogen gas using heterogeneous catalysts provides methanol together with water as well as formic acid and formaldehyde. As the generation of needed hydrogen from water or still existing hydrocarbon sources, primarily methane is highly energy consuming, the production of methanol with equimolar amount of water as well as other side products from carbon dioxide is not practical. No efficient ways for the selective high yield, high selectivity economical chemical conversion of carbon dioxide to methanol alone is presently known. High selectivity laboratory reduction of carbon dioxide to methanol was achieved only with complex metal hydrides, such as lithium aluminum hydride which is extremely costly and therefore not suited for the bulk production of methanol.

Attempts have been made to chemically convert $CO_2$ to methanol and subsequently to a hydrocarbon by catalytic or electrochemical hydrogenation. Catalysts based on metals and their oxides, in particular copper and zinc, have been developed for this process. These catalysts are unexpectedly similar to the ones currently used for the conventional methanol production via syn-gas. It is now realized that methanol is most probably formed almost exclusively by hydrogenation of $CO_2$ contained in syn-gas on the surface of the catalyst. To be converted to methanol, CO present in the syn-gas first undergoes a water gas shift reaction to form $CO_2$ and $H_2$, and the $CO_2$ then reacts with hydrogen to produce methanol. One of the limiting factors for large scale use of such methanol conversion process is the availability of the needed $CO_2$ and $H_2$. While $CO_2$ can be obtained relatively easily in large amounts from various industrial exhausts, hydrogen is presently mainly produced from fossil fuel-based syn-gas and therefore has limited availability. Further, generation of hydrogen from fossil fuels has a high energy requirement. Eventually, however, hydrogen is to be produced by electrolyzing splitting water, however, also in highly energetic processes.

Other methods for hydrogen production from fossil fuels have been investigated, including the "Carnol" process, in which thermal decomposition of methane produces hydrogen and solid carbon. The generated hydrogen is then reacted with $CO_2$ to produce methanol. This process is advantageous over methane steam reforming for requiring relatively less energy, about 9 kcal for producing one mole of hydrogen, and for producing a solid byproduct (carbon) that can be more easily handled, stored and used, compared to $CO_2$ emissions generated by methane steam reforming or partial oxidation. However, the thermal decomposition of methane requires heating it to temperatures of above 800° C. and gives only relatively low yield of hydrogen. The process, in any case, requires substantial development for commercial application.

If methanol is to be produced on a large scale from recycling carbon dioxide, such a process will be based on the abundant supply of carbon dioxide in the atmosphere and in industrial exhausts of fossil fuel power burning power plants and cement plants. It would at the same time also mitigate the greenhouse effect of $CO_2$ that is causing in a significant way the man caused global climate change (i.e., global warming). The present invention now provides such a process to obtain these benefits. Furthermore, while it is of critical importance to curtail excessive man caused carbon dioxide emissions into the atmosphere, this alone will not be sufficient to reverse the damage that has already occurred. Thus, in addition to use every method for reducing the emission of excess carbon dioxide due to human activities into the atmosphere, it would be of great benefit to also be able to remove and recycle excess carbon dioxide from the atmosphere to mitigate and reverse the harmful problem of carbon dioxide buildup in the atmosphere.

Furthermore, natural fossil fuel resources (petroleum oil, natural gas, coal, etc.) and their products are continuingly being depleted. Humankind is greatly dependent on these carbon based fossil fuels and fuel products, and their ongoing depletion from the environment results in a number of significant problems and challenges. Upon human use, fuels and fuel products are not environmentally renewed on a human time scale duration, as the combustion products carbon dioxide and water do not recycle back to form new fuels. Furthermore, carbon dioxide is a greenhouse gas, which when produced in large volumes contributes to global warming and environmental calamities.

Photosynthesis—nature's way of recycling carbon dioxide, allows plants to grow by taking in and converting carbon dioxide and water into carbohydrates in the presence of sunlight. Photosynthesic conversion of carbon dioxide from plant life to fossil fuels, however, requires the presence of vast territories of forest or agricultural land and energy, and the process is extremely slow (in the magnitude of millions of years).

Presently, the only known way to mitigate the carbon dioxide emission in fuel gases of fossil fuel burning power plants and other emission is by way of separating, collecting, and subsequently sequestering carbon dioxide in old oil field subterranean geological formations or at the bottom of the seas. Sequestration is, however, a costly process, as well as one that has only temporary mitigating effects due to the potential danger that dynamic geological events could lead to catastrophic release of large amounts of sequestered carbon dioxide, and to a renewed environmental hazard, e.g. from the suffocating effects of this dangerous gas. It is a goal of the present invention to find a practical and economical solution to overcome these problems.

SUMMARY OF THE INVENTION

Our invention relates to various embodiments of an environmentally carbon neutral use of utilizing and recycling carbon dioxide from industrial or natural sources, as well as from the air itself into methanol dimethyl ether and derived products. This method comprises separating the carbon dioxide from any available source containing same and producing methanol by reducing the carbon dioxide thus obtained under conditions sufficient to produce methanol; utilizing the methanol thus produced under conditions sufficient to generate upon its combustion energy and to chemically absorbing and recycling formed carbon dioxide in a carbon neutral cycle.

The carbon dioxide obtained from such sources is typically converted to methanol by catalytic, photochemical or electrochemical hydrogenation. The conversion to methanol, however, forms a reaction mixture also containing formic acid and formaldehyde. These can be without separation of the reaction mixture, in a subsequent treatment step conducted under conditions sufficient to produce formaldehyde and formic acid themselves converted to methanol using modifications of the so-called Canizzaro-Tischenko reactions. Converting the formaldehyde with co-formed formic acid as a hydrogen source is also feasible, without separation of the reaction mixture, into methanol, and by reacting some of the formic acid with methanol to form methyl formate, followed by hydrogenating the methyl formate under conditions sufficient to form methanol. The hydrogen needed for the hydrogenation of methyl formate can be obtained from electrolysis of water, by decomposing at least some of the formic acid from the reaction mixture or by the reaction of methane with carbon dioxide (dry reforming).

The available source of carbon dioxide is preferably an exhaust stream from a fossil fuel burning power or other industrial plants, or a natural source accompanying natural gas. These available sources would otherwise be released into the atmosphere. The utilization of the exhaust stream as a source for chemical recycling avoids emitting the carbon dioxide into the atmosphere. The available source of carbon dioxide may also the air of our atmosphere with the carbon dioxide obtained by absorbing atmospheric carbon dioxide onto a suitable adsorbent followed by treating the adsorbent to release the adsorbed carbon dioxide therefrom. By removing and recycling carbon dioxide from the atmosphere provides a source that is inexhaustible. Suitably, the adsorbent is treated by sufficient heating or is subjected to sufficient reduced pressure to release the adsorbed carbon dioxide.

The methanol that is produced can also be dehydrated under conditions sufficient to produce dimethyl ether. The dimethyl ether can be used as a suitable fuel; to be used as a substitute for Diesel fuel or household gas. Combustion of such fuel will of course generate carbon dioxide, but as carbon dioxide can be recovered and recycled for use in the production of methanol and or dimethyl ether this creates again an environmentally carbon neutral cycle. The methanol or dimethyl ether as indicated can be also utilized as convenient energy storage and transportation materials in the aforementioned cycles.

BRIEF DESCRIPTION OF THE DRAWINGS

The features and benefits of the invention will become more evident from review of the following detailed description of illustrative embodiments and the accompanying drawings, wherein.

DETAILED DESCRIPTION OF THE PREFERRED EMBODIMENTS

Figure 1:
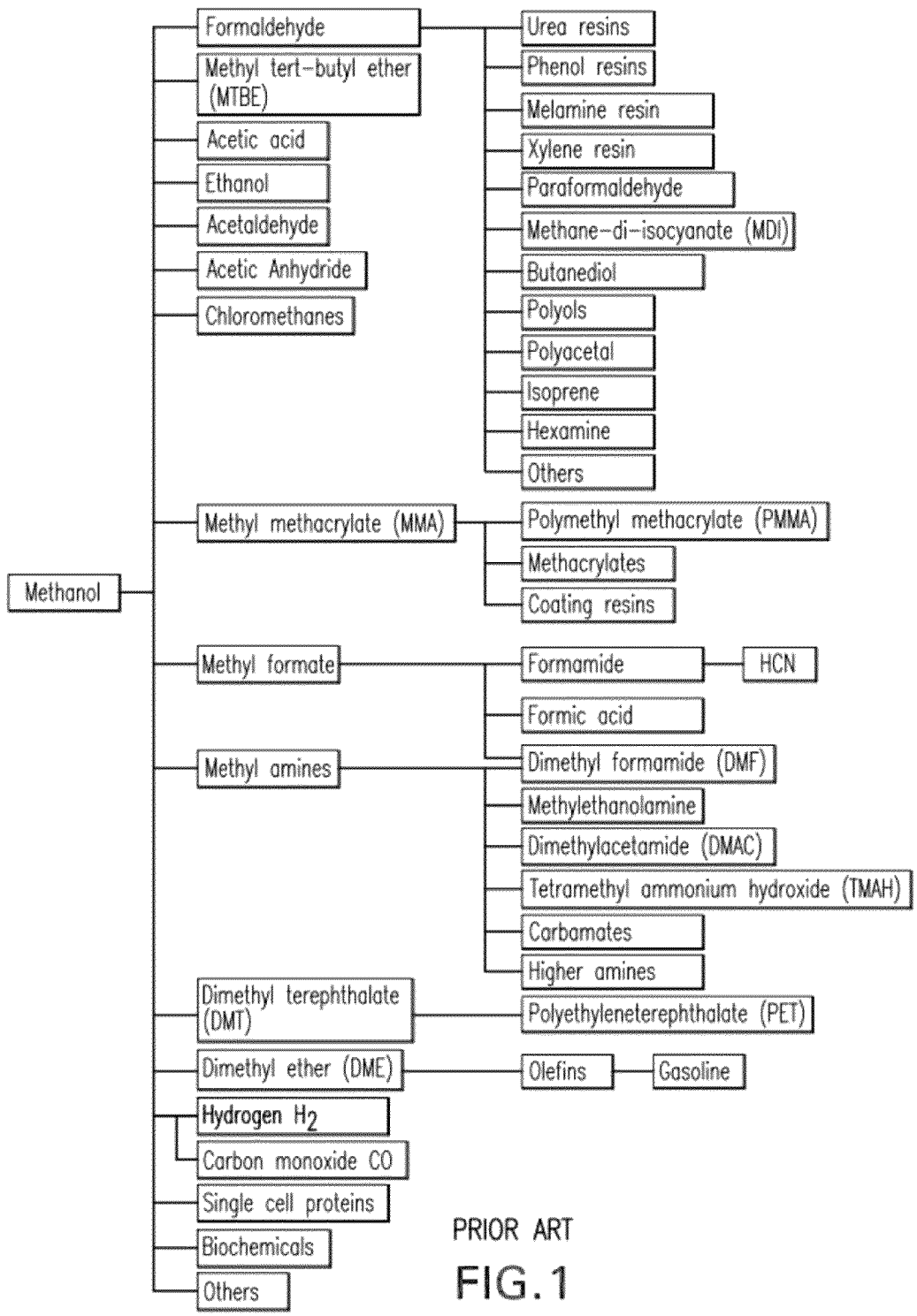
FIG. 1 shows known examples of methanol-derived chemical products and materials.
Figure 2:
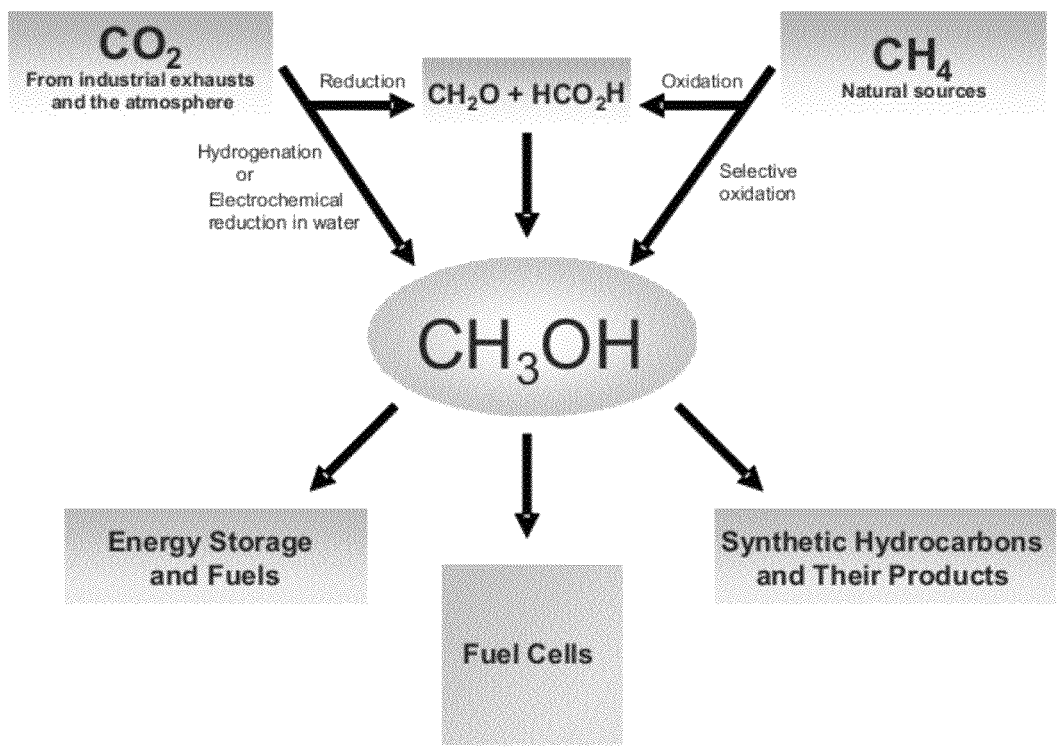
FIG. 2 schematically illustrates the present inventive process, termed the METHANOL ECONOMY and its carbon neutral chemical recycling.

The present invention relates to the efficient and economical conversion of carbon dioxide from flue gases of fossil fuel burning power plants, industrial exhaust gases, $CO_2$ accompanying natural gas or from the atmosphere itself to methanol or dimethyl ether, with their subsequent application for energy storage and transportation, fuels for internal combustion engines and fuel cells, conversion to synthetic hydrocarbons and their products, synthetic proteins and other products. The carbon dioxide to methanol conversion is a permanent, safe and economical alternative to sequestration, (underground or under the sea storage) wherein carbon dioxide through methanol is converted to useful and essential products making it a renewable general carbon source for fuels, synthetic hydrocarbons and their products.

The present invention discloses an environmentally neutral and efficient process of recycling carbon containing fuels and converting carbon dioxide formed upon their combustion or by any source to methanol. Suitable carbon dioxide sources can be industrial exhaust streams from hydrocarbon (fossil fuel) burning power plants, cement and other industrial plants, natural gas fields, under carbon dioxide accompanies the hydrocarbon gases, and the like, as well as carbon dioxide of the atmosphere itself. The use of this process of converting carbon dioxide to methanol and/or dimethyl ether and their products will also lead to a significant reduction of carbon dioxide, a major greenhouse gas, in the atmosphere thus mitigating global warming.

Carbon dioxide conversion to methanol from the mentioned generally sources also provides also formic acid and formaldehyde by either chemical, photochemical or electrochemical reduction. Formic acid and formaldehyde thus produced, in a subsequent process step, can be subsequently further substantially converted to methanol. The conversion of formaldehyde itself can be conducted in the presence of a solid supported basic catalyst or an organometallic catalyst to give methanol and formic acid, or methyl formate. Alternatively, dimerization of formaldehyde gives methyl formate, which upon catalytic hydrogenation yields methanol as the only product.

Carbon dioxide is captured and obtained from mentioned high concentration sources of its generation instead of its release into the atmosphere. Carbon dioxide can, however, also be obtained by separating it from the atmosphere itself with a suitable adsorbent (see co-pending application Ser. No. 11/780,244 filed Jul. 19, 2007) followed by desorption treatment to release the adsorbed carbon dioxide therefrom. This can be achieved by heating to release the adsorbed carbon dioxide, by treating it under reduced pressure or by a suitable combination of both.

In another embodiment of the invention to utilize needed hydrogen only in producing methanol without water as by-product, carbon dioxide is first reduced chemically, such as in its thermal reaction with carbon or electrochemically to carbon monoxide, which is subsequently catalytically converted with hydrogen to methanol.

A further route to methanol is based on the use of methane or natural gas as the hydrogen source in the reductive conversion of carbon dioxide (dry reforming) or using a suitable combination with steam reforming (wet reforming) called bi-reforming (see co-pending application Ser. No. 11/850,501 filed Sep. 5, 2007) to provide a 1:2 molar mixture of carbon monoxide and hydrogen, which subsequently can react to produce exclusively methanol. As the reforming of carbon dioxide with methane generates hydrogen, this hydrogen can also be used for the hydrogenation of methyl formate to methanol in the previously discussed embodiments.

Methanol produced according to the discussed new processes can be used for any of the practical mentioned purposes such as for energy storage and transportation, as a fuel in internal combustion engines or fuel cells, to produce derived fuels (such as dimethyl ether), dimethyl carbonate (and the like), to produce ethylene, propylene, and related for synthetic hydrocarbons and all their derived products including and not limiting single cell proteins.

The present invention relates to efficient new and economical ways of converting varied carbon dioxide sources (both containing high and low combustions) into methanol. High concentration carbon dioxide sources are those frequently accompanying natural gas in amounts typically form 2 to 35%, those from flue gases of fossil fuel (coal, natural gas, oil, etc.) burning power plants, exhaust of cement plants, fermentation plants and other industrial sources. In one embodiment of the invention carbon dioxide formed together with methanol formaldehyde and formic acid which by chemical conversion or photochemical or electrochemical reduction can further produce methanol. The invention teaches that, without separation of the product mixture in a subsequent treatment step, the mixture can be converted exclusively to methanol making the overall process both selective and high yielding. In another embodiment, reduction of carbon dioxide can give methyl formate, which is subsequently hydrogenatively converted exclusively into methanol. In a further embodiment, the chemical reduction of carbon dioxide with carbon or its electrochemical reduction produces carbon monoxide, which then is converted to methanol with utilization of needed hydrogen to form only the desired product. In this embodiment the initial reduction of carbon dioxide significantly (by a third) decreases the overall amount of hydrogen needed for producing methanol.

The present invention discloses the efficient and economical conversion of carbon dioxide, either from flue gases or fossil fuel burning power plants, from natural gas wells, varied industrial exhaust gases or from the atmosphere itself, to methanol. Both catalytic, photochemical or electrochemical reduction of carbon dioxide can be utilized with any energy source available (conventional, alternative, atomic, etc). The environmental and economic benefits of reductive chemical conversion of carbon dioxide emission instead of sequestration are a significant part of the present invention. At the same time, carbon dioxide provides a renewable source of methanol (together with dimethyl ether) that can be used for safe energy storage and transportation, production of fuels for intent combustion engine and fuel cells, feedstock for producing synthetic hydrocarbons and their products and related materials.

The use of carbon dioxide based methanol is highly desirable as it can decrease and eventually replace the world's reliance on fossil fuels. In addition, the reduction in carbon dioxide emissions as well as the removal of excess carbon dioxide from the atmosphere will assist in reducing global warming and eventual restoring atmospheric conditions to a suitable levels, thus preserving the planet's climate for future generations.

The present invention overcomes many of the difficulties in economically converting carbon dioxide to methanol. Regardless, how energy is generated, any source of energy must be stored and transported. Hydrogen claimed as the future clean energy is exceedingly difficult and intrinsically dangerous to store, handle and transport. Its conversion with $CO_2$ to methanol, a convenient liquid and derived products offers a convenient, safe way of energy storage as well as a renewable, eventually carbon natural source for synthetic hydrocarbons and their varied products.

The energy needed to generate hydrogen for catalytic or electrochemical conversion of carbon dioxide to methanol can be obtained from any available source of energy, such as still existing fossil fuels atomic, solar, wind, geothermal, etc. Photolytic, thermal, enzymatic, and other means of cleaving of water to hydrogen are also feasible.

$CO_2$ emissions from fossil fuel burning power plants and varied industries can be captured on-site. Separation of $CO_2$ from such industrial exhausts is well-developed. The major advantage in the newly disclosed chemical recycling of these sources to methanol and derived products is that carbon dioxide is not released into the atmosphere and serves as renewable carbon source for fuels and varied essential products.

The separation and use of atmospheric $CO_2$ allows chemical recycling of $CO_2$ as a renewable and unlimited source of carbon. $CO_2$ absorption facilities can be placed proximate to a hydrogen production site to enable subsequent methanol synthesis. Although the $CO_2$ content in the atmosphere is low (only 0.037%), the atmosphere offers an abundant and unlimited supply when $CO_2$ is recycled. For using atmospheric carbon dioxide efficiently, $CO_2$ absorption facilities are needed. This can be addressed by using efficient $CO_2$ absorbents such as polyethyleneimines, polyvinylpyridines, polyvinylpyrroles, etc., on suitable nano-structured solid carriers (e.g., active carbon, polymers, silica or alumina), which allow absorption of even the low concentration of atmospheric $CO_2$ (see co-pending patent application Ser. No. 11/780,244 filed Jul. 19, 2007). $CO_2$ can also be captured using basic absorbents such as calcium hydroxide ($Ca(OH)_2$) and potassium hydroxide (KOH), which react with $CO_2$ to form calcium carbonate ($CaCO_3$) and potassium carbonate ($K_2CO_3$), respectively. $CO_2$ absorption is an exothermic reaction, which liberates heat, and is readily achieved by contacting $CO_2$ with an adequate base. After capture, $CO_2$ is recovered from the absorbent by desorption, through heating, vacuum (or reduced pressure) or electrochemical treatment. Calcium carbonate, for example, is thermally calcinated to release carbon dioxide. As desorption is an endothermic, energy-demanding step, the appropriate treatment can be chosen to optimize absorption and desorption with the lowest possible energy input. Thus, $CO_2$ can be recycled by operation of absorbing-desorbing columns in convenient cycles with modest heating and/or under reduced pressure to cause desorption of $CO_2$ to take place.

When methanol, methanol-derived fuels or synthetic hydrocarbons are combusted (oxidatively used), they release $CO_2$ and water, thus providing the basis for a reversible methanol cycle, the artificial version of the natural photosynthetic recycling of $CO_2$. In contrast to the nonrenewable fossil fuel sources such as oil, gas, and coal recycling carbon dioxide from industrial and natural sources to produce methanol not only addresses the problem of diminishing fossil fuel resources by providing an unexhaustible carbon source, but also helps alleviate global warming due to greenhouse effect, which is significantly caused by mankind's activity that is increasing the carbon dioxide content in the atmosphere.

The effective hydrogenative recycling of carbon dioxide disclosed herein provides new methods of producing methanol in an improved, efficient, and environmentally beneficial way, while mitigating $CO_2$ caused climate change (global warming). The use of methanol and derived dimethyl ether as energy storage and transportation materials eliminates many difficulties excessive cost and danger of using hydrogen for such purposes. They are also excellent transportation fuels and convenient raw materials for producing synthetic hydrocarbons and their related products. The economy, safety and versatility of methanol makes the disclosed recycling of carbon dioxide further desirable.

As known in the art, methanol can be easily treated to produce varied derived compounds including dimethyl ether, produced by dehydration of methanol, and dimethyl carbonate, produced by reaction of the methanol by oxidative carbonylation. Methanol and methanol-derived compounds, e.g., DME and DMC as oxygenated fuels, can be easily blended with gasoline and used in internal combustion or Diesel engines with only minor modifications. For example, methanol can be added to gasoline up to 85% by volume to obtain commercially viable M20 or M85 fuels. Methanol can also be used to generate electricity in fuel cells, by either first catalytically reforming methanol to $H_2$ and CO or by reacting methanol directly with air in our co-invented direct methanol fuel cell (DMFC) (see U.S. Pat. No. 5,928,806). DMFC greatly simplifies the fuel cell technology and makes it readily available to a wide range of applications, including portable mobile electronic devices and electricity generators.

In addition to being a convenient safe energy storage and transportation material and fuel, methanol and methanol-derived DME are useful starting materials for various chemicals such as formaldehyde, acetic acid, and varied other products including polymers, paints, adhesives, construction materials, synthetic chemicals, pharmaceuticals, single cell proteins and the like.

Methanol and/or dimethyl ether can also be conveniently converted in a single catalytic step to ethylene and/or propylene (e.g., in the methanol to olefin or MTO process), the building blocks for producing synthetic hydrocarbons and their products.

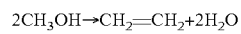

$2CH_3OH \rightarrow CH_2=CH_2+2H_2O$

$3CH_3OH \rightarrow CH_3CH=CH_2+3H_2O$

This means that the hydrocarbon fuels and products currently derived from oil and natural gas can be obtained from methanol, which itself can be obtained from the chemical recycling of natural or industrial $CO_2$ sources. A further utilization of methanol can be ready conversion to ethanol via hydration of derived ethylene. The overall conversion is

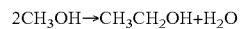

$2CH_3OH \rightarrow CH_3CH_2OH+H_2O$

Many further applications are known and can be applied to carbon dioxide derived methanol. It should be emphasized that there is no preference for any particular energy source needed for producing methanol. All sources, including still existing fossil fuels alternative sources and atomic energy can be used. Energy once produced must be, however, stored and transported, for which methanol is preferred in contrast to difficult to handle and essentially hazardous hydrogen.

The improved and efficient selective conversion of carbon dioxide, which can be from atmospheric or industrial exhaust sources, to methanol according to the present invention also provides the needed raw material for what is now termed as the METHANOL ECONOMY process. This allows convenient storage and transport of energy as a convenient, safe liquid product that can be used as a fuel in internal combustion engines or in fuel cells and as a starting material for synthetic hydrocarbons and their varied products. The METHANOL ECONOMY process encompasses both the efficient direct conversion of still available natural gas resources to methanol or dimethyl ether (as disclosed in U.S. patent application Ser. No. 11/402,051 filed Apr. 12, 2006, the entire content of which is incorporated herein by reference thereto) with first producing syn-gas as well as the presently disclosed reductive chemical conversion of carbon dioxide. The concept of the METHANOL ECONOMY process presents significant advantages and great economic possibilities. In the METHANOL ECONOMY process, methanol is used as (1) convenient energy storage medium, which allows convenient and safe storage and handling; (2) readily transported and dispensed fuel, including for internal combustion engines and methanol fuel cells; and (3) feedstock for synthetic hydrocarbons and their products currently obtained from oil and gas resources, including polymers and even single cell proteins, which can be used for animal feed or human consumption. The environmental benefits obtained by disclosed chemical recycling of carbon dioxide results in mitigating the global warming to ensure the well being of future generations.

As methanol is readily dehydrated to dimethyl ether, the disclosed conversion of carbon dioxide to methanol is also adaptable to produce dimethyl ether for fuel and chemical applications as previously noted.

The disclosed new efficient production and recycling of methanol from industrial or natural carbon dioxide sources, or even from the air itself, provides the needed raw material for replacing the diminishing fossil fuel through the METHANOL ECONOMY process. The conversion of carbon dioxide to methanol requires significant energy, which can be provided by any energy source including offpeak electric power of fossil fuel (e.g., coal) burning power plants, atomic energy or any alternative energy sources (solar, wind, geothermal, hydro, etc.). As indicated, energy generated must be conveniently stored and transported. The conversion of $CO_2$ to methanol allows storage and transportation of energy as a liquid product in an economic and safe way much more suitable than highly volatile hydrogen gas. Methanol and/or dimethyl ether are efficient fuels for internal combustion engines or direct oxidation methanol fuel cells (DMFC as well as raw materials for olefins, synthetic hydrocarbons and other products). The present invention significantly extends the scope of the utilization of carbon dioxide for the production of methanol and/or dimethyl ether from natural or industrial sources, even to the air itself.

Using the previously described principles of the invention, a new and inventive way is now disclosed to render fossil fuels and their products renewable on the human time scale and environmentally carbon neutral on combustion, allowing the mitigation of excess carbon dioxide and the prevention of its build up in the atmosphere to counteract the resultant global warming effects, through the use of new useful fuels and products and the recycling of the emissions from the combustion of such fuels and products.

The present invention describes a process for effective environmental recycling of carbon dioxide and methanol. Without being limiting, this process ensures extraction of carbon dioxide, its conversion to methanol and/or dimethyl ether, energy production obtained from the use of methanol and/or dimethyl ether, further extraction of the carbon dioxide bi-product obtained in the energy-generating methanol and/or dimethyl ether reaction, and repeating a desired number of times in cycles the above sequence of steps. Even if initial, temporary carbon dioxide storage would be affected by sequestration to develop, such stored $CO_2$ can subsequently conveniently used to produce methanol.

In these embodiments, the carbon dioxide can be obtained from any available source disclosed herein, such as, without being limiting. These include high $CO_2$ containing emissions of power plants burning fossil fuels, fermentation processes, calcination of limestone, other industrial or natural sources, as well as even the low $CO_2$ content of the atmosphere. In any embodiment, the methanol in the present invention can be obtained from any available source, such as, without being limiting, the processes described in the present application, alternative agricultural and live sources, or any other industrial or naturally occurring process.

In a preferred embodiment of the invention, the carbon dioxide source is an exhaust stream from fossil fuel burning power or industrial plant, or a source accompanying natural gas. A non-limiting utility of the present invention is in connection with coal and other fossil fuel burning power plants and industries producing large amounts of carbon dioxide. After obtaining and separating from the source, and withdrawing from sequestration storage facilities, the carbon dioxide is then subjected to hydrogenative chemical conversion to form methanol, and/or, in subsequent reaction or reactions, to further form dimethyl ether or other carbon based fuels and products. The energy required for the process can come from any suitable energy source, including, but not limited to, excess energy from fossil burning power plants in off peak use periods, alternative energy sources, atomic energy sources, etc. Various energy sources are well known in the art. On combustion of the carbon based fuels and products, the released carbon dioxide bi-product is then converted again to methanol, as described above, and the cycle is repeated a desired number of times.

In an alternative embodiment of the invention, the carbon dioxide source is the air of our atmosphere. The carbon dioxide is separated and absorbed by using means either disclosed in the art and/or described in the present application, and it is then recycled, as described in the foregoing sections.

EXAMPLES

The following examples illustrate but not limit the utility of the present process. They are based on the use of known suitable or modified chemical reactions that are applied to the processes of the invention.

Example 1

Carbon dioxide in water is known to be electrochemically reduced to formic acid and formaldehyde with methanol formed in smaller amounts while avoiding methane formation in aqueous media over Sn, Pb, In, Zn, Au, Cu, Pd and related electrodes at room temperature in the range of 40-90% current efficiency.

The above mentioned product mixture containing formic acid and formaldehyde when passed over a supported basic catalyst in a tube reactor at temperatures between 100 and 300° C. forming methanol and methyl formate in overall yield of 40 to 50%.

Example 2

Carbon dioxide is reacted with a suitable carbon source (such as charcoal and the like) at temperatures of 550 to 900° C. to produce carbon monoxide in what is called the Boudouard reaction. CO then is reacted with methanol to give methyl formate and catalytically hydrogenative converted to produce a doubled amount of methanol.

Example 3

Carbon dioxide is electrochemically reduced to carbon monoxide and subsequently is reacted further as in Example 7.

Example 4

The methyl formate obtained by the processes of Examples 1-3 is catalytically reduced with molecular hydrogen in the gas phase over copper chromite or noble metal catalysts at atmospheric pressure in the temperature range of 100-230° C. Selectivity to methanol is >90% and methyl formate conversion is about 85 to 90%. A similar reductive conversion can also be achieved electrochemically.

Example 5

Methyl formate is catalytically reduced with formic acid over Pt/C, Rh/C, Ru/C, copper chromite and the like catalyts in the gas phase at atmospheric pressure in the temperature range of 100-200° C. Selectivity to methanol is over 70-90% and methyl formate conversion is 50% in a single pass.

Example 6

Methane is reformed with carbon dioxide and (dry reforming) steam (wet reforming) in proportions to give a 1:2 mixture of carbon monoxide and hydrogen under conditions of our co-pending "bi-reforming" Patent applications. This mixture is subsequently used to produce methanol according to the equation $CO+2H_2 \rightarrow CH_3OH$. The carbon monoxide formed can also reacted as in examples 1-3 with methanol to give methyl formate, which according to Examples 4 and 5 can be hydrogenatively converted doubling the amount of methanol under moderate temperatures and pressures.

These examples illustrate the general utility of the present process of carbon dioxide to methanol conversion but skilled practitioners can utilize the disclosure and teachings provided herein to generate a suitable variation thereof. The process allows production of derived fuels, products thereof and other applications reducing or replacing reliance on fossil fuels. At the same time it also safeguards the environment by significantly reducing carbon dioxide emissions and the presence of harmful lighter carbon dioxide content in the atmosphere. The present invention provides a convenient way to recycle carbon dioxide to either prevent its emission into the atmosphere or to remove part of it from the atmosphere to generate a renewable fuel such as methanol or dimethyl ether.

Example 7

$CO_2$ is electrochemically reduced in aqueous solutions over gold and related catalysts at the cathode to CO and also $H_2$ (by concomitant electrolysis). The CO and $H_2$ mixture (syngas) is catalytically converted to methanol (see co-pending bireforming application).

What is claimed is:

1. An environmentally beneficial method of preparing a renewable fuel, which method comprises:
   obtaining carbon dioxide from a natural or chemical source that would otherwise be present in or discharged into the atmosphere; and
   producing an energy storage and transportation material or a fuel sufficient to generate energy by hydrogenatively converting the carbon dioxide thus obtained under conditions sufficient to produce methanol as the material or fuel.

2. The method of claim 1, wherein the methanol is produced by reducing the carbon dioxide under conditions sufficient to produce a reaction mixture containing formic acid with concomittant formation of formaldehyde and small amounts of methanol and methane, followed, without separation of the reaction mixture, by a treatment step conducted under conditions sufficient to convert the formaldehyde to formic acid and methanol.

3. The method of claim 2, wherein the methanol is produced by generating carbon monoxide from the carbon dioxide through a high temperature reaction with carbon, reacting the carbon monoxide with the previously produced methanol under conditions sufficient to form methyl formate, followed by catalytically hydrogenating the methyl formate under conditions sufficient to form additional methanol.

4. The method of claim 1, wherein the methanol is produced by reducing the carbon dioxide under conditions sufficient to produce a reaction mixture containing formic acid with concomittant formation of formaldehyde and small amounts of methanol and methane, augmenting the reaction mixture by reacting, without separation of the reaction mixture, the formaldehyde into methanol with some of the formic acid used as a hydrogen source, and reacting some of the formic acid with methanol to form methyl formate, followed by catalytically hydrogenating the methyl formate under conditions sufficient to form methanol.

5. The method of claim 1, which further comprises transporting the thus produced methanol fuel to a facility where the fuel is to be combusted to generate energy.

6. The method of claim 5, which further comprises combusting the methanol fuel in a power plant to form an exhaust stream that contains carbon dioxide, and recovering the carbon dioxide of the exhaust stream for use as the chemically recyclable source of carbon dioxide for preparing additional fuel.

7. The method of claim 1 wherein the methanol is produced by hydrogenatively converting the carbon dioxide to form a reaction mixture that contains methanol, formic acid and formaldehyde, followed, without separation of the reaction mixture, by a treatment step conducted under conditions sufficient to convert the formaldehyde and formic acid to methanol.

8. The method of claim 7, which comprises reacting the formaldehyde with the co-formed formic acid as a hydrogen source, without separation of the reaction mixture, into methanol, including reacting of the formic acid with methanol to form methyl formate, followed by hydrogenating the methyl formate under conditions sufficient to form double the starting amount of methanol.

9. The method of claim 8, wherein the hydrogen needed for the hydrogenation of methyl formate is obtained at least in part from cleavage of the formic acid from the reaction mixture.

10. The method of claim 1, wherein the hydrogen needed for the hydrogenative conversion of carbon dioxide is obtained by the reforming of methane or natural gas or by electrolysis of water using an available energy source.

11. The method of claim 1, which further comprises combusting the fuel to form an exhaust stream that contains carbon dioxide and in a manner that allows collection of the exhaust stream, and recovering the carbon dioxide of the exhaust stream for use as the chemically recyclable source of carbon dioxide for preparing additional fuel.

12. The method of claim 10, wherein the exhaust stream is obtained by combusting the fuel in a fossil fuel burning power or industrial plant.

13. The method of claim 1, which further comprises dehydrating the methanol under conditions sufficient to produce dimethyl ether; using the dimethyl ether as the fuel or as a component of the fuel.

14. The method of claim 13, which further comprises utilizing. as the convenient energy storage and transportation materials, the methanol or dimethyl ether in order to minimize or eliminate the disadvantages or dangers inherent in the use and transportation of hydrogen, LNG or LPG.

15. An environmentally beneficial method of preparing a renewable fuel, which method comprises:
  obtaining carbon dioxide from a natural or chemical source; and
  producing an energy storage and transportation material or a fuel sufficient to generate energy by hydrogenatively converting the carbon dioxide thus obtained under conditions sufficient to produce methanol as the material or fuel.

16. The method of claim 15, wherein the chemical source is an exhaust stream collected from the burning or combustion of a fossil fuel.

17. The method of claim 15, wherein the natural or chemical source of carbon dioxide is the atmosphere, an exhaust stream from a power or industrial plant, or a source accompanying natural gas.

18. The method of claim 15, wherein the carbon dioxide is captured and obtained from the source and is converted under conditions sufficient to produce a reaction mixture containing formic acid with concomittant formation of formaldehyde and small amounts of methanol and methane, followed, without separation of the reaction mixture, by a treatment step conducted under conditions sufficient to convert the formaldehyde to formic acid and methanol.

19. The method of claim 15, wherein the carbon dioxide is captured and obtained from the source and is reduced under conditions sufficient to produce a reaction mixture containing formic acid with concomittant formation of formaldehyde and small amounts of methanol and methane, augmenting the reaction mixture by reacting, without separation of the reaction mixture, the formaldehyde into methanol with some of the formic acid used as a hydrogen source, and reacting some of the formic acid with methanol to form methyl formate, followed by catalytically hydrogenating the methyl formate under conditions sufficient to form methanol.

20. An environmentally beneficial method of reducing the carbon dioxide content of the atmosphere by recycling carbon dioxide and producing methanol using a reductive conversion of an available source of carbon dioxide from a natural or chemical source, which method comprises:
  (A) reducing the carbon dioxide under conditions sufficient to produce a reaction mixture containing formic acid with concomittant formation of formaldehyde and small amounts of methanol and methane, followed, without separation of the reaction mixture, by a treatment step conducted under conditions sufficient to convert the formaldehyde to formic acid and methanol; or
  (B) augmenting the reaction mixture of (A) by reacting the formaldehyde with some of the formic acid as a hydrogen source, without separation of the reaction mixture, into methanol, and by reacting some of the formic acid with methanol to form methyl formate, followed by catalytically hydrogenating the methyl formate under conditions sufficient to form methanol; or
  (C) generating carbon monoxide from the carbon dioxide through a high temperature reaction with carbon, reacting the carbon monoxide with methanol produced in (A) under conditions sufficient to form methyl formate, followed by catalytic hydrogenation of the methyl formate under conditions sufficient to form methanol.

\* \* \* \* \*